United States Patent [19]

Dobson et al.

[11] 4,215,137

[45] Jul. 29, 1980

[54] METHOD OF ALLEVIATING DISEASES BY CELL-MEDIATED IMMUNE MODULATION

[75] Inventors: Richard A. Dobson, Schodack; John R. O'Connor, Cohoes, both of N.Y.

[73] Assignee: Sterling Drug Inc., New York, N.Y.

[21] Appl. No.: 919,224

[22] Filed: Jun. 26, 1978

[51] Int. Cl.$^2$ ............................................. A61K 31/40
[52] U.S. Cl. ................................................... 424/274
[58] Field of Search ........................................ 424/274

[56] References Cited

U.S. PATENT DOCUMENTS

| 3,906,092 | 9/1975 | Hilleman et al. | 424/89 |
| 3,919,411 | 11/1975 | Glass et al. | 424/81 |
| 3,920,811 | 11/1975 | Lund | 424/88 |
| 4,051,147 | 9/1977 | Johnson | 260/326.47 |
| 4,138,405 | 2/1979 | Johnson | 260/326.5 C |

FOREIGN PATENT DOCUMENTS 816542 6/1973 Belgium .

OTHER PUBLICATIONS

Journal of Infectious Disease, vol. 132, No. 5, Nov. 1975 pp. 578-581.
JAMA 232: 1052-1054, Jun. 9, 1975.
British Medical Journal, 1975, 3, 461-464.
Lancet, Feb. 21, 1976, pp. 393-395.
Transplantation, vol. 5, No. 4, Part 2, 1967, pp. 996-1000.
Immunology, Abstract 5239 (1977).

*Primary Examiner*—Leonard Schenkman
*Attorney, Agent, or Firm*—William G. Webb; B. Woodrow Wyatt

[57] ABSTRACT

Method for alleviating diseases in animals susceptible to treatment via stimulation of the cell-mediated immune system and compositions useful therefor.

14 Claims, No Drawings

METHOD OF ALLEVIATING DISEASES BY CELL-MEDIATED IMMUNE MODULATION

BACKGROUND OF THE INVENTION (a) Field of the Invention

This invention relates to a method for alleviating diseases in animals which are susceptible to treatment by stimulation of the cell-mediated immune response system comprising administering to a diseased animal a 1-substituted-pyrrole derivative and to compositions useful therefor.

(b) Description of the Prior Art

The use of immuno modulators which affect the immune response system in such a way as to combat diseases in animals which are susceptible to treatment by immuno modulators is well known. For example, bacterial or viral infections, such as Staphylococcus aureus and Herpes simplex virus, Type 2, (HSV2), have been successfully treated with levamisole [(1)-2,3,5,6-tetrahydro-6-phenylimidazo[2,1-b]thiazole; Fischer et al., J. Infect. Diseases, 132, 578–581 (1975)]. The remission or control of certain forms of cancer has been achieved with BCG vaccine (Bacillus of Calmette and Guerin, a strain of Mycobacterium bovis) [Holmes et al., J.A.M.A., 232, 1052–1055 (1975)], an immunologic adjuvant, or with levamisole [Brit. Med. Jour., 3, 461–464 (1975)], whose immuno stimulant properties in other areas is well known as indicated above. Levamisole has also been shown to have some effect in the treatment of rheumatoid arthritis by stimulation of cell-mediated immunity [Huskisson et al., The Lancet, I, 393–395 (1976)].

Other immuno stimulants disclosed by the art are: "a ... water-soluble substantially neutral polymer of acrylic acid cross-linked with ... polyalkyl-sucrose or polyalkylpentaerythritol ... "

[Lund, U.S. Pat. No. 3,920,811, patented Nov. 18, 1975]; a nucleotide or complex of polynucleotides [Hilleman et al., U.S. Pat. No. 3,906,092, patented Sept. 16, 1975]; and "a macromolecular synthetic resin complexing material such as an acrylic acid polymer cross-linked with a polyalkyl saccharide ... "

[Glass et al., U.S. Pat. No. 3,919,411, patented Nov. 11, 1975].

The 1-substituted-pyrrole derivatives used in the practice of this invention having the formulas I, II, III and IV below have been disclosed, together with their in vitro antibacterial activity in Belgian Pat. No. 816,542, and each of the compounds of Formulas I, II, III, IV and V, and the anti-tubercular activity of two of them, i.e. Compounds I and III, have been disclosed in Johnson U.S. Pat. No. 4,051,147, as well as in divisional application thereof, Ser. No. 730,162, filed Oct. 7, 1976, and now U.S. Pat. No. 4,138,405. Compounds I, II, III and V are claimed in U.S. Pat. No. 4,138,405, and Compound IV is claimed in U.S. Pat. No. 4,051,147. The compounds are disclosed in both U.S. Pat. No. 4,051,147 and U.S. Pat. No. 4,138,405 to be useful as in vitro antibacterial agents against a variety of microorganisms. Two of the species (Compounds I and III) are also there disclosed to be effective against systemic Mycobacterium tuberculosis infections on oral administration, and Compounds III, IV and V are further there disclosed to be useful as urinary antiseptic agents on oral administration in mice.

However, there has been no indication or suggestion in the prior art that Compounds I, II, III, IV, and V have immuno stimulating properties.

Natural cellular immunity in the normal host is known to be initiated by contact between an invading foreign antigen (bacteria, virus, protozoa, neoplastic cell, etc.) and thymus-derived lymphocytes (T-cells) which, when stimulated by foreign antigen, release soluble factors (lymphokines) into circulation. These factors or enzymes produced by the T-cells in turn activate the macrophages which destroy the invading organism by a process of phagocytosis followed by a direct attack on the organism by enzymes that dissolve the invading organism (lysosomal enzymes). Organisms such as tubercle bacilli and leprosy bacilli survive phagocytosis and even multiply within nonactivated macrophages. The activated macrophage however destroys these organisms by increased concentrations of lysosomes and lysosomal enzymes [Bennett et al., J. Transplantation, 5, 996–1000].

When the normal host is exposed to overwhelming numbers of invading organisms or its immune response system has been compromised by a deficiency in the immune system, only immune stimulation from sources outside the host can prevent a takeover by the intruder.

In the case of alleviation of allergic or inflammatory diseases, diabetes or essential hypertension, the role of immuno stimulators is less clear. Inflammatory conditions, such as rheumatoid arthritis, are characterized by proliferation in the affected joints of lysozomal enzymes possibly produced in the phagocytic process by the macrophage cells. Alleviation of the inflammatory condition may, in certain conditions, involve suppression, rather than stimulation, of the immune system by the immuno modulator. Thus the same chemical entity may appear to exhibit immuno stimulation as well as immuno depression of the immune response system, depending upon the particular disease condition being alleviated, and it may be more accurate to refer to such entities as immuno modulators rather than immuno stimulants or immuno suppressants, since they are usually capable of behaving in both capacities. (See for example the references given above with respect to use of levamisole as an immuno modulator.)

Chemically induced diabetes in mice or rats has been associated with impairment of cell mediated immunity (Brown et al., T-Cell Function in Diabetic Mice, [Paper No. 5239] Proc. Ann. Meeting Fed. Am. Soc. Exp. Biol. and Med., Chicago, Ill., 1976). This involvement of cellular immunity or the modification of the disease by immuno modulation is not only unexpected but unexplainable with our present knowledge.

SUMMARY

This invention relates, in a method aspect, to a method of alleviating diseases in animals which are susceptible to treatment by stimulation of the cell-mediated immune response system comprising orally administering to a diseased animal an effective amount of 1,1'-(1,4-benzoquinon-1-yldiimino)dipyrrole, 1,1'-[(1,4-phenylene)diamino]dipyrrole, 1-(1,4-benzoquinon-1-ylimino)pyrrole, 1-(4-hydroxyphenylamino)pyrrole or 1-(phenylamino)pyrrole.

In a composition of matter aspect, the invention relates to compositions for alleviating diseases in animals which are susceptible to treatment by stimulation of the cell-mediated immune response system which comprises 1,1'-(1,4-benzoquinon-1,4-yldiimino)dipyrrole, 1,1'-[(1,4-phenylene)-diamino]dipyrrole, 1-(1,4-benzoquinon-1-ylimino)pyrrole, 1-(4-hydroxyphenylamino)pyrrole or 1-(phenylamino)pyrrole in a pharmaceutical carrier.

DETAILED DESCRIPTION INCLUSIVE OF THE PREFERRED EMBODIMENTS

More specifically, this invention provides a method for alleviating diseases in animals which are susceptible to treatment by stimulation of the cell-mediated immune response system which comprises administering to a diseased animal an effective amount of 1,1'-(1,4-benzoquinon-1,4-yldiimino)dipyrrole (Compound I), 1,1'-[(1,4-phenylene)diamino]-dipyrrole (Compound II), 1-(1,4-benzoquinon-1-ylimino)pyrrole (Compound III), 1-(4-hydroxyphenylamino)pyrrole (Compound IV) or 1-(phenylamino)pyrrole (Compound V) having the respective formulas:

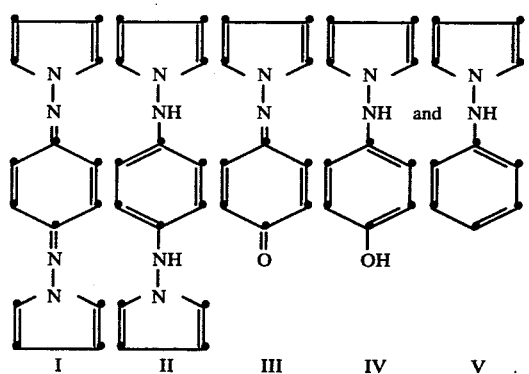

It has been surprisingly found that Compounds I, II, III, IV and V are effective in alleviating a variety of diseases in animals which are susceptible to treatment by stimulation of the immune response system. This discovery indicates usefulness of the compounds of the invention against a variety of animal diseases which are susceptible to treatment with immuno stimulants, including diseases of bacterial origin, such as leprosy caused by *Mycobacterium leprae;* diseases of viral origin, such as Herpes infections; diseases involving inflammatory conditions, such as rheumatoid arthritis, allergic encephalitis, *lupus erythematosus,* Masugi nephritis or Crohn's disease; diseases involving allergic reactions, such as allergic asthma, diseases involving protozoal infections, such as toxoplasmosis and leishmaniasis; and diseases of unknown etiology in which cell mediated immunity has been suggested or described, such as diabetes, essential or spontaneous hypertension, various neoplastic diseases and multiple sclerosis.

Diseases of many of these types have been treated with varying degrees of success with immuno stimulants. See for example Blanden et al., J. Exp. Med., 129, 1079 (1969) [treatment of *Listeria monocytogenes* infections with BCG]; Gaugas et al., Nature, 219, 408–409 (1968) [treatment of leprosy]; Fischer et al., Pediat. Res. 8, 1974 [treatment of brucella infections]; Kint et al., New Eng. J. Med. 291, 308 (1974) [treatment of *Herpes-virus labialis* infections]; Huskisson et al., The Lancet, I, 393–395 (1976) and Schuermans, The Lancet, I, 111 (1975) [treatment of rheumatoid arthritis]; Symoens et al., Brit. Med. J. IV, 592 (1974) [treatment of aphthous stomatitis]; Bertrand et al., Nouv. Presse méd., 3, 2265 (1974) [treatment of Crohn's disease]; Fischer et al., J. Infect. Diseases, 132, 578–581 (1975) [treatment of protozoal infections]; and Holmes et al., J.A.M.A., 232, 1052–1055 (1972), Study Group for Bronchogenic Carcinoma, Brit. Med. Jour. 3, 461–464 (1975), and Carter, Amer. Sc., 64, 418–423 (1976) [treatment of cancer] for examples of the use of various immuno stimulants in the treatment of diseases of the above-indicated types.

Moreover, multiple sclerosis, a disease in which the myelin sheath that insulates the nerves of the brain and spinal chord is attacked by the individuals own macrophages and antibodies, is an outstanding example of diseases caused by deficiencies in the cell mediated immune system. Such diseases may also be influenced by the immune modulation activities of the subject compounds.

In any event, with a knowledge of the mechanisms involved in modulation of the immune response system as described in the Description of the Prior Art section above at hand, compounds which owe their activity against disease conditions to their ability to modulate the immune response system can be distinguished from compounds which owe their effectiveness to a direct action on a pathogenic microorganism, for example, by use of experiments designed to test the behavior of the compounds against any of the above-indicated parameters involved in the immune response system.

Thus the immuno modulator properties of the compounds of the present compositions have been established by the following experiments.

(1) Although Compounds I and II are equally active in vitro against the *Mycobacterium tuberculosis* H37Rv organism (3.1 mcg./ml.), Compound I is very effective against systemic mouse infections produced by the intravenous inoculation of the same strain of *M. tuberculosis,* whereas Compound II is totally inactive against this infection. Absorption from the intestinal tract does not appear to be a factor, because Compound II is found in high levels in the circulatory system of orally medicated, *M. tuberculosis* infected mice. Compounds III and IV are also equally active against the TB organism in vitro (25 mcg./ml.), but against the systemic infection in mice, Compound III is four times more effective than Compound IV. Compound V is inactive against TB both in vitro and in vivo, although it is metabolized to Compound IV by the animals, as indicated by the appearance of Compound IV in the urine of mice that have been medicated orally with Compound V.

Compounds III and IV are just as active in vitro against *Staphylococcus aureus* as they are against the *M. tuberculosis* organism. However, both compounds are completely inactive against systemic infections in mice produced by this same *Staphylococcus aureus* with equal medication regimens for both infections. It is an accepted fact that systemic infections caused by *Staphylococcus aureus,* because of the rapid development of high titers of circulating antistaphylococcal antibodies, are affected by humoral and not cellular immunity.

(2) The dose-response curves for Compounds III and IV against systemic tuberculosis infections is bell-shaped, i.e. effectiveness of the compounds increases with increasing doses to an optimum dose level and then decreases with increasing dosage. Toxicity is not a factor in the latter decline in activity. This behavior indicates that the compounds do not act directly on the organism but rather act via some other biological system. On the other hand, isoniazid, which acts directly upon the invading organism, possesses a linear dose-response curve, which flattens out at the 100% effective dose and remains flat at increasing doses up to the toxic dose where mortality of the host occurs through drug toxicity.

(3) The direct involvement of the thymus and stimulation of T-cells either in the thymus or in peripheral blood on oral administration of the compounds of the invention was shown by the following tests:

(a) The thymi of mice medicated with the compounds of the invention are enlarged over either infected or non-infected, unmedicated controls, whereas the thymi of isoniazid-medicated animals are not substantially different from uninfected, unmedicated controls, thus indicating stimulation of the thymus by the compounds of the invention and the lack of such stimulation by isoniazid.

(b) Depletion of T-cell population by the administration of anti-T-cell serum has the effect of cancelling out the effectiveness of the compounds of the invention against systemic tuberculosis infections. On the other hand, administration of anti-T-cell serum to isoniazid or rifamycin treated animals infected with tuberculosis, both of which drugs owe their anti-TB activity to their ability to attack the invading microorganism directly, produced almost no diminution in the effectiveness of the test compounds.

(4) The activation of macrophages as one of the parameters in the immune response system, which are in turn modulated by the subject compounds, was shown by an experiment in which T-cell stimulation in tuberculosis infected animals by the subject compounds was markedly reduced by administration of anti-macrophage serum which substantially reduced the effectiveness of the compounds of the invention against systemic tuberculosis infections. On the other hand, anti-macrophage serum has virtually no effect on the effectiveness of isoniazid in the treatment of tuberculosis infected animals.

(5) The anti-TB activities of the compounds of the invention are markedly reduced by the administration of trypan blue, a result which is believed due to inhibition of trypan blue of lysosomal enzymes produced by the macrophages [Beck et al., Science, 157: 1180–1182 (1967)]. On the other hand, the anti-TB activity of isoniazid is only moderately diminished by trypan blue.

(6) Similarly the anti-TB activities of the compounds of the invention are blocked by simultaneous administration of dexamethasone, an adrenocortical steroid which is known to destroy leucocytes [Eisen, Immunology, Harper and Row Publishers, 2nd Ed., pages 473–474 (1974)].

(7) Finally, although the compounds of the invention possess no intrinsic anti-viral activity, yet they protect mice from challenge with *Herpesvirus hominis*. Certain of the compounds have furthermore been found to alleviate inflammatory arthritic conditions, to lower blood pressure and to lower blood glucose levels in animal models. The mechanisms that control recovery from Herpes infections require participation of cellular immunity, and as indicated above the test results against arthritic, hypertensive and hyperglycemic conditions are not inconsistent with the involvement of cell-mediated response.

The compounds of the invention can be formulated for use by preparing a dilute solution in an organic medium in which the compounds are soluble, for example ethyl alcohol, or they can be formulated in conventional carriers, including sugars such as sucrose, lactose or maltose, for oral administration as tablets or capsules.

BIOLOGICAL TEST RESULTS

The general in vitro anti-bacterial activities of the compounds of the invention were determined using standard serial dilution procedures. Results so obtained are given in Table 1 below, the results being expressed in terms of the Minimum Inhibitory Concentration (MIC) in mcg./ml. The letters (a), (b), (c), (d), (e), (f), (g), (h) and (i) designate, respectively, the organisms *S. aureus* Smith, *E. coli* Vogel, *E. coli* 198, *K. pneumoniae* 39645, *Pr. mirabilis* MGH-1, *Pr. vulgaris* 9920, *Ps. aeruginosa* MGH-2, *Strep. pyogenes* C203 and *M. tuberculosis* H37Rv.

Table 1

| Compound No. | (a) | (b) | (c) | (d) | (e) | (f) | (g) | (h) | (i) |
|---|---|---|---|---|---|---|---|---|---|
| I | >31.3 | >31.3 | >31.3 | >31.3 | >31.3 | >31.3 | >31.3 | >31.3 | 3.1 |
| II | >125 | >62.5 | >125 | >62.5 | >125 | >125 | >62.5 | >62.5 | 3.1 |
| III | 31.3 | >62.5 | >62.5 | >62.5 | 125 | 125 | >62.5 | 31.3 | 6.25 |
| IV | 31.3 | >62.5 | >125 | >125 | 125 | 125 | >62.5 | 31.3 | 6.25 |
| V | >125 | >62.5 | >125 | >125 | >125 | >125 | >62.5 | >62.5 | 3.1 |

The effectiveness of the compounds of the invention against systemic *Mycobacterium tuberculosis* infections when administered orally to mice was shown by a test procedure in which mice were infected by intravenous innoculation of 0.1 cc. of a 2 mg. (moist weight)/cc. suspension of *M. tuberculosis*, strain H37Rv grown in Youman's medium for two weeks at 37.5° C. The test animals were then treated daily with graded oral doses of the test compound for four weeks, and all mice, regardless of whether they died of the infection during the experiment or were sacrificed at the termination of the experiment, were autopsied at the time of death. At autopsy, the TB lung lesions were scored and given one of the following numerical values:

0 = (normal lung)
15 = ± (lung congestion and enlargement-no lesions)
33 = + (lung congestion and enlargement-few small lesions)
66 = + + (TB lesions cover 50% of the lungs)
100 = + + + (TB lesions cover 100% of the lungs).

A drug regimen that produces a survival rate of 90% to 100% and an average lung score of 25 or lower is considered to be outstandingly active. The results are given in Table 2 along with data for isoniazid, which is included for purposes of comparison. The data are given in each case in terms of the % survival (hereinafter % S), the lung score (hereinafter L.S.) and also in terms of the ratio of the lung score of control animals to the lung score of the test animals (hereinafter the C/T ratio). The higher this ratio, the more effective the test compound is considered to be.

Table 2

| Medication | Dose in mg./kg./day | | | | | | |
|---|---|---|---|---|---|---|---|
| | 0 | 5 | 3.1 | 6.25 | 12.5 | 25 | 50 |
| In- fec- | | | | | | | |

Table 2-continued

| Medication | Dose in mg./kg./day | | | | | |
|---|---|---|---|---|---|---|
| | 0 | 5 | 3.1 | 6.25 | 12.5 | 25 | 50 |
| ted Control | 0% (96.6) | | | | | | |
| Isoniazid | | 100% (16.8) 5.75 | | | | | |
| Cpd. I | | | 20% (84.8) 1.14 | 40% (55.8) 1.73 | 100% (28.8) 3.35 | 100% (18.6) 5.19 | 100% (21.9) 4.10 |
| Cpd. II | | | 20% (89.9) 1.07 | 0% (81.5) 1.19 | 40% (73.2) 1.32 | 40% (73.2) 1.32 | |
| Cpd. III | | | 30% (71.3) 1.35 | 10% (83.1) 1.16 | 40% (34.2) 2.82 | 50% (40.8) 2.38 | 60% (32.4) 2.98 |
| Cpd. IV | | | 30% (60.9) 1.59 | 80% (27.3) 3.54 | 90% (22.2) 4.35 | 70% (27.3) 3.54 | 0% (52.8) 1.83 |
| Cpd. V | | | | | | | 10% (93.3) 1.04 |

Using the same test procedure as that described above in connection with the data presented in Table 2, the fact that the compounds of the invention are active in vivo against TB infections in mice only when administered orally was shown by the data presented in Table 3 below where the routes of administration (oral, subcutaneous and intraperitoneal) are indicated by the respective designations p.o., s.c. and i.p., and where as before %S and L.S. represent percent survival and lung score, respectively, and C/T is the ratio of the lung score of control and test animals.

Table 3

| Cpd. | Dose | P.O. | | | S.C. | | | I.P. | | |
|---|---|---|---|---|---|---|---|---|---|---|
| | | % S | L.S. | C/T | % S | L.S. | C/T | % S | L.S. | C/T |
| I | 3.125 | 50 | 37.5 | 2.58 | 30 | 71.3 | 1.35 | 20 | 59.7 | 1.62 |
| I | 6.25 | 60 | 33.9 | 2.85 | 30 | 89.9 | 1.07 | 0 | 66.4 | 1.45 |
| I | 12.5 | 100 | 22.2 | 4.35 | 10 | 66.0 | 1.46 | 0 | 54.2 | 1.78 |
| I | 25 | 100 | 18.6 | 5.19 | 10 | 84.7 | 1.14 | 10 | 54.3 | 1.78 |
| I | 50 | 100 | 16.8 | 5.75 | 20 | 66.1 | 1.46 | 50 | 40.7 | 2.37 |
| III | 3.125 | 30 | 79.6 | 1.26 | 30 | 73.1 | 1.37 | 60 | 32.5 | 3.1 |
| III | 6.25 | 80 | 30.6 | 3.27 | 50 | 59.3 | 1.69 | 60 | 47.5 | 2.1 |
| III | 12.5 | 70 | 37.5 | 2.80 | 40 | 62.6 | 1.60 | 50 | 49.5 | 2.01 |
| III | 25 | 70 | 34.0 | 2.94 | 10 | 86.5 | 1.16 | 0 | 40.8 | 2.45* |
| III | 50 | 100 | 25.2 | 3.97 | 10 | 86.5 | 1.16 | 0 | 30.6 | 3.27* |

*Toxic levels i.p. - mice died before lesions could develop.

Some data obtained in tests on the compounds of the invention indicate, but fail to completely establish, that the compounds are metabolized in the animal body. Thus in urinary antisepsis tests, the compounds of the invention were administered orally to groups of three normal rats at a dose level of 100 mg./kg. Half of the dose was given in the morning and the other half eight hours later. The rats were placed in metabolism cages after the first medication, and the pooled urine from the three rats were collected for twenty-four hours after the first medication. The urine was sterilized by membrane filtration and tested for antibacterial activity against standard screening organisms. The Maximum Inhibitory Dilution (MID) of the urine against each organism is given in Table 4 where as before the organisms *S. aureus* Smith, *E. coli* Vogel, *E. coli* 198, *K. pneumoniae* 39645, *Pr. mirabilis* MGH-1, *Pr. vulgaris* 9920 and *Ps. aeruginosa* MGH-2 are identified by the letters (a), (b), (c), (d), (e), (f) and (g), respectively.

Table 4

| Organism | Cpd. I | Cpd. II | Cpd. III | Cpd. IV | Cpd. V |
|---|---|---|---|---|---|
| (a) | 1:8 | 1:8 | 1:32 | 1:64 | 1:32 |
| (b) | <1:2 | <1:2 | <1:2 | <1:2 | <1:2 |
| (c) | | | | 1:32 | 1:128 |
| (d) | <1:2 | <1:2 | <1:2 | <1:2 | <1:2 |
| (e) | 1:16 | 1:8 | 1:4 | 1:16 | 1:32 |
| (f) | <1:2 | <1:2 | <1:2 | <1:2 | <1:2 |
| (g) | <1:2 | <1:2 | <1:2 | <1:2 | <1:2 |

Comparison of these data with that shown in Table 1 shows that in the urinary antisepsis test, certain of the compounds, especially Compounds I, II and V display an entirely different profile of in vitro activity against the same series of microorganisms than found in the earlier tests, thus indicating that metabolites in the urine are involved.

A further indication that a metabolite of Compounds I, III and IV may in some way be involved in the immune response mechanism is provided by data obtained showing that the anti-TB activity of the compounds can be blocked by intraperitoneal injection of 30 mg./kg./dose two times a day of SKF 525A [2-diethylaminoethyl-α,α-diphenylvalerate hydrochloride], a compound which interferes with the metabolism of other administered compounds by inhibition of liver microsomal enzymes [Rogers et al., J. Pharmacol. Exptl. Therap. 146, 286–293 (1964)]. Data so obtained which show the blocking effect of SKF 525A on the anti-TB activity of each of Compounds I, III and IV, but not that of isoniazid, which does not act by cell-mediated immunity, are given in Table 5 where as before %S and L.S. represent % survival and lung score, respectively.

Table 5

| | Control | | Cpd. I* | | Cpd. III* | | Cpd. IV* | | Isoniazid* | |
|---|---|---|---|---|---|---|---|---|---|---|
| | % S | L.S. | % S | L.S. | % S | L.S. | % S | L.S. | % S | L.S. |
| (A) | 5 | 96.6 | 100 | 16.8 | 100 | 18.6 | 60 | 46 | 100 | 15.0 |
| (B) | 10 | 96.6 | 40 | 66.3 | 50 | 69.7 | 20 | 79.7 | 90 | 27.3 |

(A) Without SKF 525A
(B) With SKF 525A 30 mg./kg./dose B.I.D.
*12.5 mg./kg./day divided Using a high pressure liquid chromatographic assay method sensitive to 0.007 mcg./ml. no levels of Compound I could be detected in the blood plasma of mice that had been orally medicated daily for four weeks with dose levels of 3.1, 6.25, 12.5 and 25 mg./kg./day of the compound, doses that were found to be highly effective against tuberculosis infections. These results demonstrate that the alleviation of the tuberculosis disease condition is not attributable to Compound I as such.

The structures of any metabolites that may be produced from any of the subject compounds have not been determined, and in fact it is not known whether the immune stimulation produced by the compounds is due to the structures themselves or to some metabolite.

Further evidence for the oral activity of Compounds I, III and IV against *M. tuberculosis* infections was obtained by administration of the compound to guinea pigs infected with *M. tuberculosis* H37Rv using the same procedure as described above in connection with the data presented in Table 2 recording results obtained in mice. However, since TB infections in guinea pigs produce lesions which, rather than being confined to the lungs as in mice, are produced throughout the body, especially in the spleen, the liver, the lungs and the lymph nodes, a different scoring system for each of these organs is used based on the same scale as used in the mouse model described above, and a total score for the test animals is calculated as the sum of the individual organ scores. Data so obtained on Compounds I and III and for isoniazid (designated "Ref.") are given in Table 6. As before doses are expressed in mg./kg., and %S represents percent survivors.

Table 6

| Cpd. | Dose | % S | Organ Score | | | | |
|------|------|-----|--------|-------|------|---------------|-------|
| | | | Spleen | Liver | Lung | Lymph Node | Total |
| Control | — | 44.6 | 20.7 | 14.3 | 15.0 | 11.7 | 61.7 |
| I | 6.25 | 80 | 12 | 8 | 10 | 5 | 35 |
| I | 12.5 | 80 | 8 | 6 | 6 | 6 | 26 |
| I | 25 | 100 | 8 | 9 | 5 | 3 | 25 |
| I | 50 | 60 | 0 | 0 | 2 | 2 | 4 |
| III | 6.25 | 80 | 12 | 11 | 7 | 6 | 36 |
| III | 12.5 | 100 | 26 | 17 | 10 | 9 | 62 |
| III | 25 | 80 | 11 | 9 | 6 | 7 | 33 |
| III | 50 | 60 | 9 | 11 | 6 | 7 | 33 |
| Ref. | 1.5 | 100 | 5 | 5 | 4 | 7 | 13 |
| Ref. | 3.1 | 100 | 2 | 3 | 6 | 2 | 13 |
| Ref. | 6.25 | 80 | 1 | 1 | 3 | 0 | 5 |
| Ref. | 12.5 | 80 | 0 | 0 | 2 | 0 | 2 |

Although two of the compounds of the invention (III and IV) have been shown to be as active in vitro against *Staphylococcus aureus* as they are against the TB organism, they are inactive on in vivo administration against staphylococcus infections in mice, a further indication that the compounds do not either act as such directly on the organism or do not activate the humoral immune system and thus that they likely act by stimulation of the cell-mediated immune system. Data so obtained, expressed in terms of number of survivors out of a total test group at given dose levels, are given in Table 7 below.

Table 7

| Cpd. | Dose mg/kg./day | M. tuberculosis | S. aureus |
|------|-----------------|-----------------|-----------|
| III | 3.1 | 0/10 | |
| III | 6.25 | 6/10 | |
| III | 12.5 | 10/10 | |
| III | 25 | 10/10 | |
| III | 50 | 10/10 | 0/10 |

Table 7-continued

| Cpd. | Dose mg./kg./day | M. tuberculosis | S. aureus |
|------|------------------|-----------------|-----------|
| III | 100 | | 0/10 |
| III | 200 | | 0/10 |
| IV | 3.1 | 0/10 | |
| IV | 6.25 | 3/10 | |
| IV | 12.5 | 10/10 | |
| IV | 25 | 10/10 | |
| IV | 50 | 10/10 | 1/10 |
| IV | 100 | | 0/10 |
| IV | 200 | | 0/10 |

Stimulation of the thymus by one of the subject compounds (Compound I) when administered orally to non-infected mice in comparison with either TB infected or non-infected control mice or in comparison with isoniazid medicated non-infected controls is shown by the data given in Table 8. Compound I and isoniazid were administered at respective oral doses of 12.5 and 5 mg./kg./day for four weeks, and all animals were autopsied at the same age. As shown by the data, the thymi of mice medicated with Compound I are greatly enlarged in comparison with the thymi of either non-medicated infected or uninfected mice or when compared with non-infected isoniazid-medicated mice.

Table 8

| Cpd. | TB Infection | Thymus Ave. Wt. (mg.) |
|------|--------------|------------------------|
| None | None | 57.4 |
| I | None | 71.1 |
| Isoniazid | None | 57.2 |
| None | Yes | 38.6 |

Further evidence of the involvement of the thymus and of T-cell stimulation in the mechanism of action of the subject compounds in alleviating tuberculosis infections is shown by the data in Table 9 which shows the effect of the administration of anti-T-cell serum. The latter is an immune serum prepared by immunizing rabbits with T-cells isolated from the same strain of mice used in the TB studies. This hyperimmune serum, when injected back into mice, severely depletes the T-cell population. In this study, each of four groups of twenty tuberculosis infected mice per group were randomly divided in half. One half of each group received 0.25 ml. of anti-T-cell immune serum twice weekly for four weeks subcutaneously in addition to the anti-tuberculosis medication, and the other half received only the anti-tuberculosis medication. In Group I, none of the mice received anti-TB medication and half received anti-T-cell serum. In Groups 2, 3 and 4 all mice in each group received an oral medication of 12.5, 25 and 25 mg./kg./day of Compounds I, III and IV, respectively, and half of each of these groups received anti-T-cell serum. In Group 5 all of the mice received oral medication of isoniazid at 6.25 mg./kg./day and half received anti-T-cell serum. In Group 6, all of the mice received oral medication of rifamycin at 12.5 mg./kg./day, and half of the group received anti-T-cell serum. Compound I, when administered at 12.5 mg./kg./day for a four week period, produced 100% survival and a lung score of 15 (no visible TB lesions), but when anti-T-cell serum was administered to the other half of this group, the survival rate dropped to 20%, and the lung score soared to 89.9. Similarly, Compound III administered at 25 mg./kg./day for four weeks produced 80% survival and a lung score of 40.4, but administration of anti-T- cell serum to the other half caused the survival rate to drop to 30% and the lung score to more than double to 86.6. Compound IV administered at 25 mg./kg./day for four weeks produced a 60% survival rate and a lung score of 54.3, while administration of anti-T-cell serum to the other half of this group caused the survival rate to drop to 20% and the lung score to almost double to 83.3. These data thus clearly demonstrate that the anti-tuberculosis activities of Compounds I, III and IV is virtually eliminated by the simultaneous administration of anti-T-cell immune serum. In contrast, neither isoniazid nor rifamycin, two well known anti-TB drugs which directly inhibit the organism, lose activity on simultaneous administration of anti-T-cell serum to the infected animals. The data so obtained are given in Table 9 below.

Table 9

| Drug Regimen | Anti-T-Cell Serum | % S | L.S. | Thymus Ave. Wt. (mg.) |
|---|---|---|---|---|
| Infected Control | None | 0 | 100 | 38.6 |
|  | 2 × weekly | 0 | 96.6 | 12.4 |
| Cpd. I | None | 100 | 15 | 128.8 |
|  | 2 × weekly | 20 | 89.9 | 17.9 |
| Cpd. III | None | 80 | 40.4 | 96.4 |
|  | 2 × weekly | 30 | 86.6 | 18.3 |
| Cpd. IV | None | 60 | 54.3 | 85.4 |
|  | 2 × weekly | 20 | 83.3 | 18.7 |
| Isoniazid | None | 100 | 15 | 117.6 |
|  | 2 × weekly | 100 | 20.4 | 89.7 |
| Rifamycin | None | 90 | 18.6 | 98.2 |
|  | 2 × weekly | 90 | 30.3 | 64.8 |

Evidence that the subject compounds are involved in the stimulation of macrophages through the immune system is provided by the data presented in Table 10 which shows the inhibitory effect on the anti-TB activity of the compounds of the invention by the administration of anti-macrophage serum. Antimacrophage serum (AMS) was administered at 0.15 ml./dose (i.p.) at two and one days prior to TB infection and at two, five and eight days post infection. The procedure used is similar to that used in the anti-T-cell serum test described above.

Table 10

| Medication | Dose | Ave. Days Surv. | %S | L.S. | C/T |
|---|---|---|---|---|---|
| Infected Controls | — | 24.3 | 40 | 80 | 1.04 |
| AMS Infected Controls | — | 24.3 | 40 | 83.1 | — |
| AMS + Cpd. I | 12.5 | 25.1 | 50 | 58 | 1.45 |
| AMS + Cpd. III | 2.5 | 25 | 50 | 61 | 1.36 |
| AMS + Isoniazid | 6.25 | 31 | 100 | 15 | 5.54 |

As shown by the data, neither Compound I nor Compound III produce any improvement in the survival rate of TB infected mice treated with AMS at doses previously found to be effective against this infection. In contrast, the effectiveness of isoniazid against TB infection is in no way diminished by administration of AMS.

Evidence of the involvement of macrophages in the anti-TB activity of one of the subject compounds is also shown by experiments in which administration of trypan blue, a macrophage toxin, markedly reduces the anti-TB activity of Compound I in tuberculosis infected mice. In contrast, the activity of isoniazid, whose anti-TB activity does not depend on involvement of macrophages and the immune system, is only moderately affected by trypan blue administration. Data so obtained are given in Table 11. The trypan blue was administered at a dose of 4 mg. two times a week intraperitoneally, while the reference drug, isoniazid, was administered at 5 mg./kg./day for four weeks. As before %S, L.S. and C/T represent percent survivors, lung score and the ratio of the lung score in control to test animals, respectively. Administration of trypan blue is indicated in the column headed Tr. Bl.

Table 11

| Medication | Dose (mg./kg.) | Tr. Bl. | % S | L.S. | C/T |
|---|---|---|---|---|---|
| Infect. Controls | — | No | 0 | 100 | — |
| Isoniazid | 5 | No | 100 | 15 | 6.67 |
| Trypan Blue | — | Yes | 10 | 93.2 | 1.07 |
| Isoniazid | 5 | Yes | 90 | 33.9 | 2.95 |
| Cpd. I | 6.25 | No | 70 | 47.4 | 2.11 |
| Cpd. I | 12.5 | No | 100 | 16.8 | 5.95 |
| Cpd. I | 25 | No | 100 | 16.8 | 5.95 |
| Cpd. I | 6.25 | Yes | 40 | 73 | 1.28 |
| Cpd. I | 12.5 | Yes | 70 | 76 | 1.22 |
| Cpd. I | 25 | Yes | 80 | 52.8 | 1.77 |

As can be seen, the trypan blue had only moderate effect on either the survival rate or the lung scores in animals administered isoniazid, while administration of trypan blue with Compound I dramatically reduced the effectiveness of the latter.

Further studies have shown that trypan blue, either alone or in combination with Compound I, enhances phagocytic activity. This is demonstrated by measuring the rate of clearance of radio labelled colloid from test animals administered either trypan blue, Compound I alone or trypan blue and Compound I together and comparing the results with those obtained with unmedicated controls. The procedure used is described as follows:

Sprague-Dawley rats, weighing 200 g. were lightly anesthetized with pentobarbital, and a gelatinized lipid emulsion with a $^{131}I$ label was injected at a dose of 50 mg./kg. via tail vein and blood samples taken at two minute intervals for the first ten minutes. After a lapse of fifteen minutes from the time of administration of the radio labelled emulsion, the animals were killed, and the liver, lungs and spleen removed, weighed and tissue samples of each taken for determination of the amount of colloid present. A Baird-Atomic gamma counter was employed to assess radioactivity of the blood and tissue samples so that blood clearance rates and tissue deposition on a per gram and total organ basis could be determined. As shown by the data in Table 12 below, Compound I at either 3, 20 or 50 mg./kg./day (p.o.) enhanced clearance rates of the colloid. However trypan blue, either alone or in combination with Compound I, accelerated the rate of clearance even more, thus indicating enhanced phagocytic activity by the combination of Compound I and trypan blue (T.B.).

Table 12

| Medication | Days | Clearance ($t_{\frac{1}{2}}$) | % Injected Drug In: Liver | Lung | Spleen |
|---|---|---|---|---|---|
| Control |  | 10.27 | 49.09 | 0.89 | 5.40 |
| Trypan Blue | 7 | 8.94 | 44.79 | 1.81 | 3.06 |
| Trypan Blue | 14 | 7.08 | 71.14 | 1.99 | 4.51 |
| Trypan Blue | 20 | 9.46 | 76.00 | 0.78 | 4.23 |
| Trypan Blue | 28 | 8.81 | 63.40 | 0.84 | 6.38 |
| Cpd. I | 8 | 7.26 | 58.29 | 0.77 | 4.36 |
| Cpd. I | 15 | 10.35 | 55.17 | 1.10 | 6.49 |
| Cpd. I | 22 | 8.59 | 60.10 | 0.84 | 5.83 |
| Cpd. I | 29 | 9.68 | 52.27 | 0.92 | 4.63 |
| Cpd. I + T.B. | 7 | 6.83 | 75.06 | 1.89 | 1.65 |
| Cpd. I + T.B. | 14 | 7.02 | 70.03 | 0.85 | 4.48 |
| Cpd. I + T.B. | 21 | 8.13 | 55.86 | 0.68 | 3.90 |

Table 12-continued

| Medication | Days | Clearance (t½) | % Injected Drug In: Liver | Lung | Spleen |
|---|---|---|---|---|---|
| Cpd. I + T.B. | 28 | 7.83 | 59.96 | 0.82 | 5.58 |

Reduction in the number of leucocytes, including macrophages and T-lymphocytes, in *M. tuberculosis* infected mice medicated with the subject compounds was also shown by studies in which subcutaneous administration of either 1 mg./kg./day or 10 mg./kg./day of dexamethasome (Dexa.) was shown to sharply inhibit the anti-TB activity of Compound I in comparison with either non-dexamethasone medicated controls or isoniazid-medicated animals. The data so obtained are given in Table 13.

Table 13

| Medication | Dose | Dose Dexa. | % S | L.S. | C/T |
|---|---|---|---|---|---|
| Infected Cont. | — | — | 5 | 100 | — |
| Isoniazid | 5 | — | 100 | 15.0 | 6.66 |
| Cpd. I | 6.25 | — | 60 | 50.8 | 1.97 |
| Cpd. I | 12.5 | — | 100 | 18.6 | 5.38 |
| Cpd. I | 25 | — | 90 | 18.6 | 5.38 |
| Dexa. | — | 1 | 0 | 100 | 1.0 |
| Isoniazid | 5 | 1 | 100 | 15.0 | 6.66 |
| Cpd. I | 6.25 | 1 | 10 | 96.6 | 1.03 |
| Cpd. I | 12.5 | 1 | 30 | 93.2 | 1.07 |
| Cpd. I | 25 | 1 | 100 | 40.8 | 2.45 |
| Dexa. | — | 10 | 10 | 100 | 1.0 |
| Isoniazid | 5 | 10 | 90 | 16.8 | 5.95 |
| Cpd. I | 6.25 | 10 | 40 | 78.8 | 1.28 |
| Cpd. I | 12.5 | 10 | 0 | 83.0 | 1.20 |
| Cpd. I | 25 | 10 | 10 | 83.0 | 1.20 |

The effectiveness of Compound I in the treatment of virus infections known to be susceptible to treatment by cell-mediated stimulation of the immune response system was shown by in vivo tests against *Herpesvirus hominis*-Type 2 although the drug has no direct effect on the same virus when tested in tissue culture medium. Thus two experiments were conducted in which mice innoculated intravaginally with *Herpesvirus hominis*-Type 2 received Compound I orally for two weeks prior to infection and continuing for two weeks post infection. The disease produced by this innoculation is evidenced by herpetic vesicles and inflammation of the vulva which appear about four days after innoculation. This is followed in two or three days by hind leg paralysis and finally death. In the first study carried out in mature mice, the infection which produced 50% mortality in the untreated controls, was lighter and more easily controlled by the drug than in the second study carried out in young mice. Thus the mice were somewhat younger and thus more susceptible to the disease in the second study. Data so obtained are given in Table 14 in terms of percent survival. From the data it will be seen that at dose levels of 6.25 to 12.5 mg./kg., dramatic improvements over controls were obtained in both studies.

Table 14

| Study No. | Control | Dose (mg./kg.) Cpd. I | | | | | | |
|---|---|---|---|---|---|---|---|---|
| | | 3.1 | 6.25 | 12.5 | 25 | 50 | 100 | 200 |
| 1 | 50 | 70 | 80 | 100 | 100 | — | — | — |
| 2 | 15 | 15 | 70 | 60 | 50 | 60 | 40 | 30 |

The effectiveness of the subject compounds in the treatment of inflammatory conditions was demonstrated by results obtained in anti-inflammatory activity tests on oral administration in mice using the carrageenin-induced foot edema test method described by Van Arman et al., J. Pharmacol. Exptl. Therap. 150, 328 (1965), a modification of the procedure described by Winter et al., Proc. Soc. Exp. Biol. Med. 111, 544 (1962), and the adjuvant-induced arthritis test described by Pierson, J. Chronic Diseases 16, 863 (1963) and Glenn et al., Am. J. Vet. Res. 26, 1180 (1965). The results so obtained are given in Table 15. Doses are expressed in terms of millimoles per kg., and the results are expressed in terms of percent inhibition of the inflammatory condition. The designations A.A. and C.E. represent the adjuvant-induced arthritis and carrageenin-induced edema tests, respectively.

Table 15

| Cpd. | Dose (mM/kg.) | A.A. | C.E. |
|---|---|---|---|
| I | 0.023 | 33* | — |
|  | 0.07 | 50** | — |
|  | 0.08 | — | 13 |
|  | 0.21 | 69** | — |
|  | 0.324 | — | 22 |
| II | 0.023 | 32** | — |
|  | 0.07 | 76** | — |
|  | 0.21 | 79** | — |
| III | 0.023 | 27 | — |
|  | 0.07 | 28* | — |
|  | 0.21 | 31* | — |
| IV | 0.023 | 28* | — |
|  | 0.07 | 21 | — |
|  | 0.21 | 15 | — |
| V | 0.023 | 23 | — |
|  | 0.07 | 25 | — |
|  | 0.21 | 58** | — |

*Statistically significant from positive controls $p \leq .05$
*Statistically significant from positive controls $p \leq .01$ Two of the subject compounds (Compounds I and II) were found to be active as antihypertensive agents on oral administration in spontaneously hypertensive rats. The spontaneously hypertensive rat (SHR) is a strain of genetically hypertensive animals developed from Wistar rats by Okamoto et al., Jap. Circ. J., 27, 282–293 (1963) after selective inbreeding. Unlike any other hypertensive animal model, the SHR requires no surgical intervention, and it is widely recognized as the closest model to essential hypertension in man. Furthermore, the hypertension in these rats is not due to any of the known causes of secondary hypertension, and the blood pressure increases progressively with age. Complications often observed in human essential hypertension such as cardiac, renal and vascular changes are also observed in the SHR. The procedure used is described as follows: Each compound to be screened is tested in five SHR's whose base line blood pressure has been determined earlier in the day. The test compounds are given orally, suspended in 1% gum tragacanth in a total volume of 1 ml./kg. Systolic blood pressure measurements at 2, 6 and 24 hours after administration of the test compound are obtained with a photoelectric tensometer (ankle rubber cuff method) as described by kersten et al., J. Lab. Clin. Med. 32, 1090–1098 (1947). Compound I suspended in gum tragacanth was administered at daily oral doses of 50 mg./kg. for twelve consecutive days, and Compound II suspended in gum tragacanth (GT) was administered at 50 mg./kg. for seven days followed by a dose of 100 mg./kg. for the next five days. A control group run side by side in each study received only the gum tragacanth. Data so obtained are given in Table 16 below, results being recorded in terms of the mean blood pressure and the scientific error for each reading.

Table 16

| Medication | Pre-Med Baseline B.P. | 1 (2) | 1 (6) | 1 (24) | 2 (2) | 2 (6) | 2 (24) | 3 (2) | 3 (6) | 3 (24) | 3' (2) | 4 (6) | 4 (24) | 5 (2) | 5 (6) | 7+ (24) | 8 (6) | 8 (24) | 9 (6) | 9 (24) | 10 (2) | 10 (6) | 10 (24) | 11 (6) | 11 (24) | 12 (2) | 12 (6) |
|---|---|---|---|---|---|---|---|---|---|---|---|---|---|---|---|---|---|---|---|---|---|---|---|---|---|---|---|
| 1%GT | 182 / 9.1 | 178 / 5.2 | 178 / 5.8 | 180 / 7.8 | 183 / 5.8 | 184 / 7.0 | 180 / 8.4 | 184 / 4.5** | 189 / 7.6 | 193 / 10. | — | 188 / 7.9* | 189 / 11.7 | 188 / 9.8 | 184 / 11.2 | 193 / 9.1 | 193 / 8.4** | 186 / 9.4** | 184 / 5.3** | 191 / 7.2** | 188 / 5.6** | 183 / 7.3** | 192 / 13.1** | 189 / 6.7 | 195 / 7.5** | 195 / 5.0 | 197 / 6.6** |
| Cpd I | 183 | 170 | 186 | 183 | 155 | 163 | 165 | — | 158 | 166 | — | 163 | 172 | 152 | 162 | 155 | 142 | 151 | 148 | 151 | 147 | 149 | 140 | 145 | 143 | | |
| 1%GT | 7.2 / 183 / 6.2 | 6.6 / 178 / 6.7 | 7.0 / 182 / 4.5 | 6.4 / 174 / 4.8 | 6.9 / 182 / 5.1 | 5.0 / 176 / 4.1 | 6.0 / 186 / 8.7 | 5.7 / 181 / 3.9* | 9.4 / 176 / 8.7 | 191 / 5.4** | 10.2 / 182 / 9.2 | 6.1 / 173 / 6.7 | 5.3 / 182 / 5.6* | 4.2 / 186 / 8.7** | 6.3 / 187 / 3.2** | 7.9 / 182 / 6.1 | 6.6 / 182 / 8.8 | 8.1 | 7.1 | 6.5 / 192 / 6.4* | 5.6 / 188 / 5.6 | 5.2 / 188 / 5.6* | 7.4 | 3.8 | 7.4 / 188 / 2.2** | 6.2 / 187 / 4.8** | 4.2 / 180 / 4.7** |
| II | 6.2 | 2.7 | 2.7 | 3.7 | 3.2 | 5.5 | 5.4 | 8.1 | 6.0 | 6.7 | 2.1 | 5.9 | 4.6 | 6.2 | 5.2 | 1.8 | 4.4 | 5.4 | — | 7.4 | 5.7 | 3.6 | — | — | 2.8 | 3.0 | 3.0 |

+Medication on weekend (Days 6 and 7) but no blood pressure measurements taken
*Significantly different from corresponding control p<0.05
**Significantly different from corresponding control p<0.01

Compound I was also found active in the adrenal-regeneration hypertensive rat test [Skelton, Proc. Soc. Exp. Biol. Med. 90, 342 (1955)]. As in the SHR test, the compound was administered at single daily doses of 50 mg./kg./day for twelve consecutive days in a gum tragacanth suspension. A control group received only the gum tragacanth. Data so obtained expressed in terms of the mean blood pressure and the scientific error for each reading are given in Table 17 below.

Table 17

| Medication | Pre-Med Baseline B.P. | 1 | | 2 | | 3 | | 4 | | 5 | | 7+[a] | 8 | | 9 | | 10 | | 11 | | 12 |
|---|---|---|---|---|---|---|---|---|---|---|---|---|---|---|---|---|---|---|---|---|---|
| | | 2 | 6 | 24 | 2 | 6 | 24 | 2 | 6 | 24 | 2 | 6 | 24 | 2 | 6 | 24 | 24 | 2 | 6 | 24 | 2 | 6 | 24 | 2 | 6 | 24 | 2 | 6 | 24 | 2 | 6 |
| 1%GT | 194 10.2 | 189 11.7 | 191 9.5 | 196 12.0 | 191 8.8 | 192 10.7 | 194 12.3 | 192 14 | 184 17.7 | 198 8.4* | 196 11 | 191 9.7* | 195 12.7 | 194 13 | 195 12.5 | 197 13.0** | 192 12.5 | 192 12.6 | 196 11.2 | 191 13.2 | 192 9.4 | 195 11.9 | 194 12.7 | 196 12.9* | 194 11.5* | 187 13.4 | 189 13.8 | 193 11** | 194 10.8** | 194 10.2 |
| Cpd I | 194 7.9 | 190 14.6 | 186 7.9 | 195 7.8 | 187 10.8 | 186 11 | 184 9.8 | 177 9.0 | 166 6.2 | 152 16.4* | 158 13 | 158 10.2* | 161 9.7 | 164 8.9 | 159 11.1 | 148 5.4* | 165 9.3 | 166 6.9 | 170 6.4 | 167 14.9 | 171 9.5 | 161 8.7* | 153 13.6* | 151 11.2* | 153 10.5* | 164 8.1 | 161 6.9 | 140 6.5** | 151 6.4** | 148 10.9* |

[a]Medication on weekend (Days 6 and 7) but no blood pressure measurements taken
*Significantly different from corresponding control p<0.05
**Significantly different from corresponding control p<0.01

The data presented in Tables 16 and 17 show that a 50 mg./kg. single daily oral dose of Compound I resulted in an anti-hypertensive effect that became apparent on the third day, and reductions in blood pressure on the model are given in Table 19. In the streptozotocin model, results are the mean±s.e. of nine rats per group, while in the alloxan model, results are the mean±s.e. of thirteen rats per group.

Table 18

| Medication | Dose | Week Post Med. Hr. | 1 | | | 2 | | | 3 | | |
|---|---|---|---|---|---|---|---|---|---|---|---|
| | | | 0 | 3 | 6 | 0 | 3 | 6 | 0 | 3 | 6 |
| 1% G.T. | — | | 358±15 | 377±18 | 351±26 | 360±13 | 376±11 | 358±13 | 367±10 | 405±8 | 375±11 |
| Cpd. I. | 12.5 | 335±13 | 342±16 | 339±14 | 326±19 | 350±20 | 346±22 | 327±15 | 366±15 | 358±12 | |
| Cpd. I | 50 | | 284±28 | 264±35 | 244±34 | 251±26 | 237±27 | 206±32 | 252±19 | 224±26 | 169±27 |
| %Δ vs. Control | | | | | | (−30%) | (−37%) | (−42%) | (−31%) | (−45%) | (−55%) |
| 1% G.T. | — | | 357±11 | 378±9 | 378±5 | 358±12 | 366±5 | 353±12 | 354±11 | 386±6 | 378±5 |
| Cpd. V | 12.5 | | 344±10 | 356±17 | 336±24 | 345±7 | 344±9 | 311±22 | 335±6 | 337±11 | 309±26 |
| Cpd. V | 25 | | 323±11 | 294±20* | 252±34** | 278±24* | 237±33* | 196±37* | 292±27 | 254±37* | 216±45* |
| %Δ vs. Control Cpd. | | | (−22%) | (−33%) | (−22%) | (−35%) | (−44%) | (−18%) | (−34%) | (−43%) | |
| Cpd. V | 50 | | 335±8 | 282±17** | 236±30** | 278±29 | 202±37** | 217±41* | 203+33** | 147±22** | 121±24** |
| %Δ vs. Control | | | | (−25%) | (−38%) | | (−45%) | (−39%) | (−43%) | (−62%) | (−68%) |

*Significantly different from mean of vehicle control group p<0.01
**Signficantly different from mean of vehicle control group p<0.001

Table 19

| Medication | Dose | Week Post Med. Hr. | 1 | | | 2 | | | 3 | | |
|---|---|---|---|---|---|---|---|---|---|---|---|
| | | | 0 | 3 | 6 | 0 | 3 | 6 | 0 | 3 | 6 |
| 1% G.T. | | | 325±30 | 348±32 | 322±31 | 352±11 | 380±11 | 383±9 | 352±17 | 388±14 | 376±12 |
| Cpd. V | 50 | | 299±32 | 263±32 | 277±31 | 220±32* | 165±27** | 119±14** | 185±34** | 148±38 | 139±39 |
| %Δ vs. Control | | | | | | (−38%) | (−57%) | (−69%) | (−47%) | (−62%) | (−63%) |

*Significantly different from mean of vehicle control group p<0.01
**Significantly different from mean of vehicle control group p<0.001 order of 40 to 50 mm. Hg had been reached. Compound II in the same test showed somewhat the same pattern of blood pressure lowering, but the magnitude of the lowering at the end of the test period was somewhat less (i.e. 20-30 mm. Hg). In the adrenal regeneration model, Compound I at daily oral doses of 50 mg./kg. for twelve consecutive days produced an anti-hypertensive response beginning on the third day and reached a lowering of 40-50 mm. Hg below base line at the end of the study.

Certain compounds of the invention have also been found to have hypoglycemic activity in alloxan and streptozotocin-induced diabetes in rats. In the test procedures used, diabetes was produced in male, Sprague-Dawley rats weighing approximately 150 g. by the administration of either alloxan monohydrate, 160 mg./kg. (s.c.), or streptozotocin, 65 mg./kg. (i.v.), after an overnight fast. Fasting blood glucose levels were obtained once each week for three weeks using a modification of the procedure described by Hoffman, J. Biol. Chem. 120, 51(1937) which involves the measurement of the reduction of yellow ferricyanide ion to colorless ferrocyanide by glucose. Animals having fasting blood glucose levels of <250 mg./dl. for the last two weeks were distributed into groups such that all groups in a test had a similar distribution and mean fasting blood glucose level. Normal rats were similarly distributed on the basis of a single fasting blood glucose level. The test compounds were suspended in 1% gum tragacanth and administered orally in 5 ml./kg. twice a day. One group in each test was given 1% gum tragacanth as a control, and fasting blood glucose levels were determined for each group at weekly intervals.

Results, expressed in terms of mg. of blood glucose/dl., obtained in streptozotocin-treated animals are given in Table 18, and results obtained in the alloxan

We claim:

1. A method for alleviating diseases in animals, susceptible to treatment by modulation of the cell-mediated immune response system, selected from viral, inflammatory, hyperglycemic and hypertensive diseases which comprises administering orally to a diseased animal an effective amount of a compound having one of the formulas:

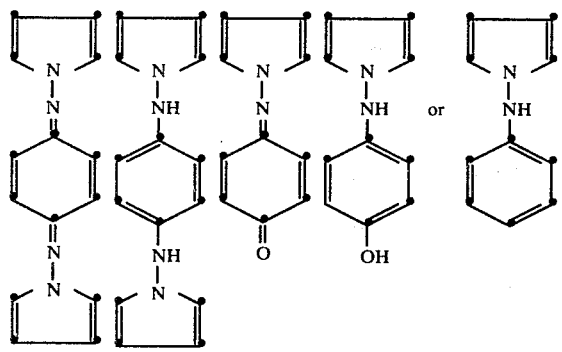

as the immuno modulating agent.

2. A method according to claim 1 for alleviating viral diseases in animals which are susceptible to treatment by modulation of the cell-mediated immune response system which comprises administering orally to a diseased animal an effective amount of a compound having the formula:

as the immuno modulating agent.

3. A method according to claim 1 for alleviating an inflammatory disease in animals which are susceptible to treatment by modulation of the cell-mediated immune response system which comprises administering orally to a diseased animal an effective amount of a compound having one of the formulas:

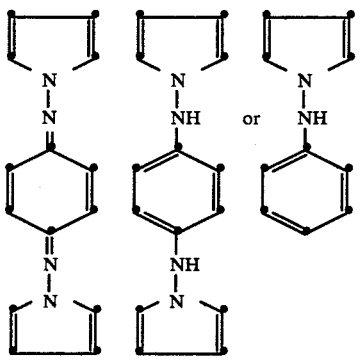

as the immuno modulating agent.

4. A method according to claim 1 for alleviating a hyperglycemic disease in animals which are susceptible to treatment by modulation of the cell-mediated immune response system which comprises administering orally to a diseased animal an effective amount of a compound having one of the formulas:

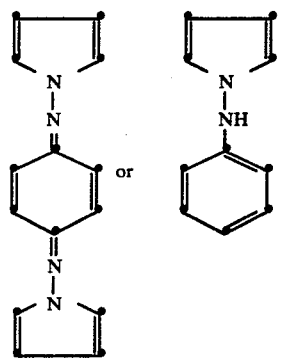

as the immuno modulating agent.

5. A method according to claim 1 for alleviating a hypertensive disease in animals which are susceptible to treatment by modulation of the cell-mediated immune response system which comprises administering orally to a diseased animal an effective amount of a compound having one of the formulas:

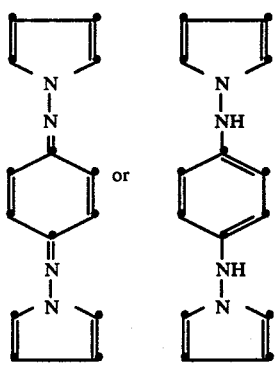

as the immuno modulating agent.

6. A method according to claim 2 for alleviating infections derived from Herpesvirus infections.

7. A method according to claim 3 for alleviating arthritic diseases.

8. The method according to claim 7 which comprises administering an effective amount of 1,1'-(1,4-benzoquinon-1,4-yldiimino)dipyrrole.

9. The method according to claim 7 which comprises administering an effective amount of 1,1'-[(1,4-phenylene)diamino]-dipyrrole.

10. The method according to claim 7 which comprises administering an effective amount of 1-(phenylamino)pyrrole.

11. A method according to claim 4 comprising administering an effective amount of 1,1'-(1,4-benzoquinon-1,4-yldiimino)dipyrrole.

12. A method according to claim 4 comprising administering an effective amount of 1-(phenylamino)pyrrole.

13. A method according to claim 5 comprising administering an effective amount of 1,1'-(1,4-benzoquinon-1,4-yldiimino)dipyrrole.

14. A method according to claim 5 comprising administering an effective amount of 1,1'-[(1,4-phenylene)-diamino]dipyrrole.

* * * * *

UNITED STATES PATENT AND TRADEMARK OFFICE
CERTIFICATE OF CORRECTION

PATENT NO. : 4,215,137

DATED : July 29, 1980

INVENTOR(S) : Richard A. Dobson and John R. O'Connor

It is certified that error appears in the above-identified patent and that said Letters Patent are hereby corrected as shown below:

Column 4, line 3, "(1972)," should read - -(1975),- -.

Column 15, replace Table 16 with the attached corrected table.

Columns 21 and 22, replace Table 18 with the attached corrected table.

Columns 23 and 24, Claims 3, 4 and 5, line 2 of each, in each instance, change "are" to --is--.

Column 23, Claim 4, line 6, change "havine" to - -having- -.

UNITED STATES PATENT AND TRADEMARK OFFICE
CERTIFICATE OF CORRECTION

PATENT NO.    : 4,215,137                    Page 2 of 3
DATED         : July 29, 1980
INVENTOR(S)   : Richard A. Dobson and John R. O'Connor It is certified that error appears in the above-identified patent and that said Letters Patent are hereby corrected as shown below:

Table 16

| Pre-Med Baseline B.P. | | 1 | | | 2 | | | 3 | | | 4 | | | 5 | | | 7+ | | 8 | | | 9 | | | 10 | | 11 | | 12 | |
|---|---|---|---|---|---|---|---|---|---|---|---|---|---|---|---|---|---|---|---|---|---|---|---|---|---|---|---|---|---|---|
| | | 2 | 6 | 24 | 2 | 6 | 24 | 2 | 6 | 24 | 2 | 6 | 24 | 2 | 6 | 24 | 2 | 6 | 24 | 6 | 24 | 2 | 6 | 24 | 6 | 24 | 2 | 6 |
| IZGT | 182 | 176 | 178 | 180 | 183 | 184 | 180 | 186 | 189 | 193 | - | 188 | 189 | 188 | 184 | 193 | 194 | 193 | 186 | 184 | 191 | 188 | 183 | 192 | 189 | 195 | 195 | 197 |
| | 9.1 | 5.2 | 5.8 | 7.8 | 5.0 | 7.0 | 8.4 | 4.5 | 7.6 | 10.3 | - | 7.9 | 11.7 | 9.8 | 11.2 | 9.1 | 7.2 | 8.4 | 9.4 | 5.3 | 7.2 | 5.6 | 7.3 | 13.1 | 6.7 | 7.5 | 5.0 | 6.6 |
| Cpd I | 183 | 182 | 182 | 183 | 170 | 186 | 183 | 153 | 163 | 165 | - | 156 | 166 | 165 | 163 | 172 | 153 | 162 | 155 | 162 | 151 | 158 | 151 | 149 | 158 | 158 | 155 | 155 |
| | 7.2 | 5.6 | 7.0 | 6.4 | 6.6 | 6.9 | 5.0 | 6.0 | 5.7 | 9.4 | - | 10.2 | 6.1 | 5.3 | 4.2 | 6.3 | 7.9 | 6.6 | 8.1 | 7.1 | 6.5 | 5.6 | 5.2 | 7.4 | 3.8 | 7.4 | 6.2 | 4.2 |
| IZGT | 183 | 178 | 182 | 174 | 178 | 182 | 176 | 186 | 181 | 176 | 191 | 182 | 173 | 182 | 186 | 187 | 182 | 182 | - | - | 192 | 188 | 188 | - | - | 188 | 187 | 180 |
| | 6.2 | 4.6 | 4.5 | 4.8 | 6.7 | 5.1 | 4.1 | 8.7 | 3.9 | 8.7 | 5.4 | 9.2 | 6.7 | 5.6 | 8.7 | 3.2 | 6.1 | 8.8 | - | - | 6.4 | 5.6 | 5.6 | - | - | 2.2 | 6.8 | 4.7 |
| Cpd II | 186 | 183 | 165 | 175 | 172 | 182 | 165 | 168 | 164 | 160 | 169 | 166 | 158 | 162 | 182 | 150 | 173 | 180 | - | - | 157 | 171 | 170 | - | - | 158 | 155 | 160 |
| | 6.2 | 2.7 | 2.7 | 1.7 | 3.2 | 5.5 | 5.4 | 8.1 | 6.0 | 6.7 | 2.1 | 5.9 | 4.6 | 6.2 | 5.2 | 1.8 | 4.4 | 5.4 | - | - | 7.4 | 5.7 | 3.6 | - | - | 2.8 | 3.0 | 3.0 |

+   Medication on weekend (Days 6 and 7) but no blood pressure measurements taken \*   Significantly different from corresponding control $p < 0.05$ \*\*  Significantly different from corresponding control $p < 0.01$

UNITED STATES PATENT AND TRADEMARK OFFICE
CERTIFICATE OF CORRECTION

PATENT NO. : 4,215,137  Page 3 of 3

DATED : July 29, 1980

INVENTOR(S) : Richard A. Dobson and John R. O'Connor

It is certified that error appears in the above-identified patent and that said Letters Patent are hereby corrected as shown below:

Table 18

| Medication | Dose | Week Post Med. Hr. | 1 | | | 2 | | | 3 | | |
|---|---|---|---|---|---|---|---|---|---|---|---|
| | | | 0 | 3 | 6 | 0 | 3 | 6 | 0 | 3 | 6 |
| 1% GT | — | | 358±15 | 377±18 | 351±26 | 360±13 | 376±11 | 358±13 | 367±10 | 405±8 | 375±11 |
| Cpd. I | 12.5 | | 335±13 | 342±16 | 339±14 | 326±19 | 350±20 | 346±22 | 327±15 | 366±15 | 358±12 |
| Cpd. I | 50 | | 284±28 | 264±35 | 244±34 | 251±26 | 237±27 | 206±32 | 252±19 | 224±26 | 169±27 |
| %Δ vs Control | | | | | | (−30%) | (−37%) | (−42%) | (−31%) | (−45%) | (−55%) |
| 1% GT | — | | 357±11 | 378±9 | 378±5 | 358±12 | 366±5 | 353±12 | 354±11 | 316±6 | 378±5 |
| Cpd V | 12.5 | | 344±10 | 356±17 | 336±24 | 343±7 | 344±9 | 311±22 | 335±6 | 337±11 | 309±26 |
| Cpd V | 25 | | 323±11 | 294±20* | 252±34** | 278±24* | 237±33* | 196±37* | 292±27 | 254±37* | 216±45* |
| %Δ vs Control Cpd | | | | (−22%) | (−33%) | (−22%) | (−35%) | (−44%) | (−18%) | (−34%) | (−43%) |
| Cpd V | 50 | | 335±8 | 282±17** | 236±30** | 278±29 | 202±37** | 217±41* | 203+33** | 147±22** | 121±24** |
| %Δ vs Control | | | | (−25%) | (−31%) | | (−45%) | (−39%) | (−43%) | (−62%) | (−68%) |

*Significantly different from mean of vehicle control group p<0.01
**Significantly different from mean of vehicle control group p<0.001

Signed and Sealed this

First Day of December 1981

[SEAL]

Attest:

GERALD J. MOSSINGHOFF

Attesting Officer     Commissioner of Patents and Trademarks